United States Patent [19]

Riebli et al.

[11] Patent Number: 4,508,731
[45] Date of Patent: Apr. 2, 1985

[54] MICROBICIDAL N-(TETRAHYDRO-2-ON-FUR-3-YL)-N-SUBSTITUTED ACETYL-ANILINES AND -NAPHTHYLAMINES

[75] Inventors: Peter Riebli, Basel; Hanspeter Fischer, Bottmingen; Rudolph C. Thummel, Courgenay; Adolf Hubele, Magden, all of Switzerland

[73] Assignee: Ciba Geigy Corporation, Ardsley, N.Y.

[21] Appl. No.: 579,230

[22] Filed: Feb. 13, 1984

Related U.S. Application Data

[62] Division of Ser. No. 370,759, Apr. 22, 1982, Pat. No. 4,448,773.

[30] Foreign Application Priority Data

Apr. 29, 1981 [CH] Switzerland ............ 2783/81

[51] Int. Cl.³ ............ A01N 43/08; A01N 43/10; C07D 307/30; C07D 309/28
[52] U.S. Cl. .................... 514/472; 514/444; 514/445; 548/262; 548/336; 548/374; 549/6; 549/8; 549/60; 549/63; 549/222; 549/320; 549/321
[58] Field of Search ............ 549/6, 8, 60, 63, 222, 549/320, 321; 548/262, 336, 374; 424/202, 203, 275, 279

[56] References Cited
U.S. PATENT DOCUMENTS
4,287,210 9/1981 Eckhardt et al. ............ 424/309

Primary Examiner—Richard L. Raymond
Attorney, Agent, or Firm—Frederick H. Rabin

[57] ABSTRACT

Compounds of the formula

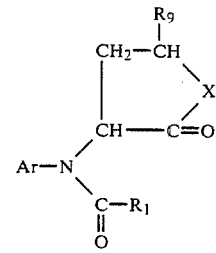

in which
Ar is 2-alkyl-, -alkoxy- or -halo-methyl-phenyl or α-naphthyl, each of which is further substituted,
$R_1$ is 2-furyl, 2-tetrahydrofuryl, alkenyl, cyclopropyl, β-alkoxyethyl, hydroxymethyl, triazolylmethyl, imidazolylmethyl, pyrazolylmethyl, alkylsulfinyl, alkylsulfonyl, alkoxy, alkenyloxy, alkynyloxy, alkylthio, alkenylthio, alkynylthio, alkylsulfinyloxy, dialkylaminosulfinyloxy, phosphoric or thiophosphoric esters or amides, or alkylcarbonyloxy, and
$R_9$ is hydrogen or methyl,
are microbicidally, in particular fungicidally active. The preferred compounds are those in which Ar is 2-methylphenyl, 2-methoxyphenyl, 2-chlorophenyl or α-naphthyl, each of which is further substituted by azido, and $R_9$ is hydrogen.

11 Claims, No Drawings

MICROBICIDAL N-(TETRAHYDRO-2-ON-FUR-3-YL)-N-SUBSTITUTED ACETYL-ANILINES AND -NAPHTHYLAMINES

This is a divisional of application Ser. No. 370,759 filed on Apr. 22, 1982, U.S. Pat. No. 4,448,773.

The present invention relates to microbicidally active acylalanine and acylnaphthylamine derivatives, to processes for producing them, to compositions containing them as active ingredients, and to the use thereof for combating fungi and bacteria.

The novel compounds correspond to the general formula I

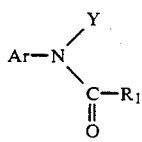

(I)

wherein
Ar is a group of the formula

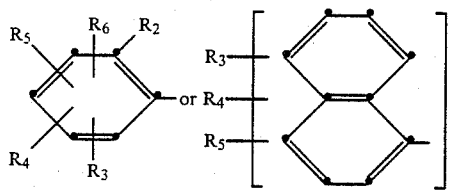

$R_1$ is 2-furyl, 2-tetrahydrofuryl, $C_2$–$C_4$- alkenyl, cyclopropyl, $\beta$-($C_1$–$C_4$) -alkoxyethyl or —$CH_2Z$, each being unsubstituted or substituted by halogen, and Z in the group —$CH_2Z$ being
(a) —OH,
(b) —1H-1,2,4-triazolyl, 1-imidazolyl or 1-pyrazolyl,
(c) —S(O)$_n$—$R_{13}$ where $R_{13}$ is $C_1$–$C_4$-alkyl, and n is 1 or 2,
(d) —X—$R_{14}$ where X is oxygen or sulfur, and $R_{14}$ is $C_1$–$C_6$-alkyl, $C_3$–$C_4$-alkenyl or $C_3$–$C_4$-alkynyl, each unsubstituted or substituted by $C_1$–$C_2$-alkoxy,
(e) —OSO$_2$—$R_{15}$ where $R_{15}$ is $C_1$–$C_4$-alkyl, or mono- or di-($C_1$–$C_3$)-alkylamine,

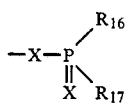

(f)

where X is oxygen or sulfur, $R_{16}$ is $C_1$–$C_4$-alkyl, $C_1$–$C_4$-alkoxy or $C_1$–$C_4$-alkylamino, and $R_{17}$ is $C_1$–$C_4$-alkoxy or $C_1$–$C_4$-alkylamino, or

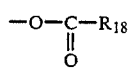

(g)

where $R_{18}$ is $C_1$–$C_3$-alkyl which is unsubstituted or substituted by $C_1$–$C_2$-alkoxy,
$R_2$ is $C_1$–$C_3$-alkyl, $C_1$–$C_3$-alkoxy or halogen,
$R_3$ is —$CH_2OH$, —$N_3$,

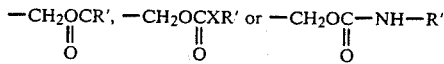

where R' is $C_1$–$C_6$-alkyl or $C_2$–$C_4$-alkenyl, each unsubstituted or substituted by halogen or $C_1$–$C_3$-alkoxy, or it is unsubstituted or substituted phenyl, and X is oxygen or sulfur,
$R_4$ is hydrogen, $C_1$–$C_3$-alkyl, $C_1$–$C_3$-alkoxy, halogen, —$NO_2$ or —$NH_2$,
$R_5$ is hydrogen or $C_1$–$C_3$-alkyl,
$R_6$ is hydrogen or $C_1$–$C_3$-alkyl,

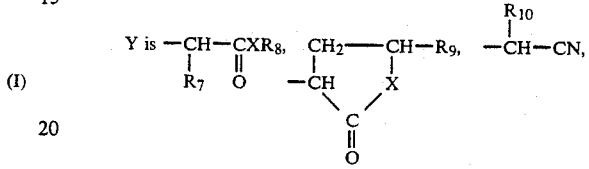

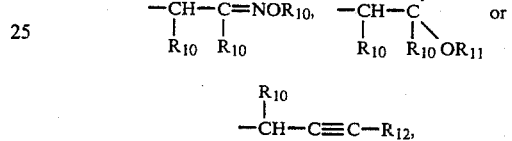

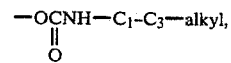

wherein $R_7$ is hydrogen, $C_1$–$C_2$-alkyl which is unsubstituted or substituted by halogen, —OH, —OC$_1$—$C_3$-alkyl or —OCNH—$C_1$–$C_3$—alkyl,
 ‖
 O $R_8$ is $C_1$–$C_4$-alkyl which is unsubstituted or substituted by $C_1$–$C_2$-alkoxy,
$R_9$ is hydrogen or methyl,
$R_{10}$ is hydrogen or $C_1$–$C_3$-alkyl,
$R_{11}$ is $C_1$–$C_4$-alkyl, whereby $R_{11}$'s together can form a $C_2$–$C_3$-alkylene bridge which is mono- or polysubstituted by $C_1$–$C_3$-alkyl,
$R_{12}$ is hydrogen, halogen, $C_1$–$C_2$-alkyl or phenyl, and X is oxygen or sulfur.

The substituents $R_3$, $R_4$ and $R_5$ of the naphthylamine derivatives embraced by the formula I fluctuate, so that each of these substituents can occupy the position 2, 3, 4, 5, 6, 7 or 8 in the naphthyl ring.

By alkyl or alkyl moiety of another substituent are meant, depending on the given number of carbon atoms, for example the following groups: methyl, ethyl, propyl and butyl, as well as isomers thereof, such as isopropyl, isobutyl, sec-butyl or tert-butyl. Alkenyl is for example: vinyl, propenyl-(1), allyl, butenyl-(1), butenyl-(2) or butenyl-(3); and alkynyl is particularly propargyl. Halogen here and in the following is fluorine, chlorine, bromine or iodine, preferably chlorine or bromine.

A preferred group of microbicides according to the invention comprises compounds of the formula I having the following combination of substituents:
$R_1$ is 2-furyl, 2-tetrahydrofuryl, $C_2$–$C_4$-alkenyl, cyclopropyl, $\beta$-($C_1$–$C_2$)-alkoxyethyl or —$CH_2$—Z, where Z is
(a) —OH,
(b) 1H-1,2,4-triazolyl or 1-imidazolyl, (c) —S(O)$_n$—R$_{13}$, where R$_{13}$ is C$_1$–C$_2$-alkyl, and n is 2, (d) —X'—R$_{14}$, where X' is oxygen or sulfur, and R$_{14}$ is C$_1$–C$_6$-alkyl, C$_3$–C$_4$-alkenyl or C$_3$–C$_4$-alkynyl, each unsubstituted or substituted by C$_1$–C$_2$-alkoxy, (e) —OSO$_2$—R$_{15}$, where R$_{15}$ is C$_1$–C$_2$-alkyl, or mono- or di-(C$_1$–C$_2$)-alkylamine,

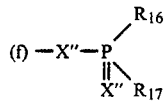

where X" is sulfur, R$_{16}$ is C$_1$–C$_2$-alkyl, C$_1$–C$_4$-alkoxy or C$_1$–C$_2$-alkylamino, and R$_{17}$ is C$_1$–C$_4$-alkoxy or C$_1$–C$_4$-alkylamino, or

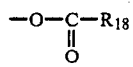

where R$_{18}$ is C$_1$–C$_2$-alkyl which is unsubstituted or substituted by C$_1$–C$_2$-alkoxy, R$_2$ is C$_1$–C$_2$-alkyl, C$_1$–C$_2$-alkoxy or halogen,
R$_3$ is —CH$_2$OH, —N$_3$,

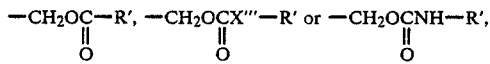

where R' is C$_1$–C$_3$-alkyl or C$_2$–C$_3$-alkenyl, each unsubstituted or substituted by chlorine or methoxy, and X''' is oxygen or sulfur, R$_4$ is hydrogen, C$_1$–C$_2$-alkyl, C$_1$–C$_2$-alkoxy, —NO$_2$ or NH$_2$,
R$_5$ is hydrogen or C$_1$–C$_2$-alkyl,
R$_6$ is hydrogen or C$_1$–C$_2$-alkyl,
Y has the meanings defined under the formula I, whereby R$_7$ is hydrogen or C$_1$–C$_2$-alkyl which is unsubstituted or substituted by halogen, —OH, —O(C$_1$–C$_2$)-alkyl or

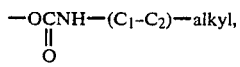

R$_8$ is C$_1$–C$_3$-alkyl which is unsubstituted or substituted by C$_1$–C$_2$-alkoxy,
R$_9$ is hydrogen,
R$_{10}$ is hydrogen or C$_1$–C$_2$-alkyl,
R$_{11}$ is C$_1$–C$_2$-alkyl, whereby R$_{11}$'s together can also be C$_2$–C$_3$-alkylene,
R$_{12}$ is hydrogen, halogen or C$_1$–C$_2$-alkyl, and
X is oxygen or sulfur.

A further preferred group of microbicides of the formula I is characterised by the following combination of substituents:

R$_1$ is 2-furyl, 2-tetrahydrofuryl, C$_2$–C$_4$-alkenyl, cyclopropyl, β-methoxyethyl or —CH$_2$Z, where Z is
(a) 1H-1,2,4-triazolyl,
(b) —S(O)$_n$—R$_{13}$, where R$_{13}$ is CH$_3$, and n is 2,
(c) —X'$^{\nu}$—R$_{14}$, where X'$^{\nu}$ is oxygen, and R$_{14}$ is C$_1$–C$_4$-alkyl, C$_3$–C$_4$-alkenyl or C$_3$–C$_4$-alkynyl, each unsubstituted or substituted by C$_1$–C$_2$-alkoxy,
(d) —OSO$_2$—R$_{15}$, where R$_{15}$ is mono-(C$_1$–C$_3$)-alkylamine,

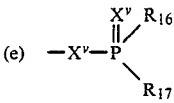

where X$^{\nu}$ is sulfur, and R$_{16}$ and R$_{17}$ independently of one another are each C$_1$–C$_3$-alkoxy, or

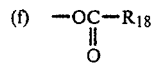

where R$_{18}$ is C$_1$–C$_3$-alkyl,
R$_2$ is methyl, methoxy or chlorine,
R$_3$ is —CH$_2$OH, —N$_3$ or

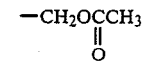

R$_4$ is hydrogen, methyl, methoxy, NO$_2$ or NH$_2$,
R$_5$ is hydrogen or methyl,
R$_6$ is hydrogen or methyl,
Y has the meanings defined under the formula I, whereby
R$_7$ is C$_1$–C$_2$-alkyl which is unsubstituted or substituted by chlorine, —OH, —OC$_1$–C$_2$-alkyl or

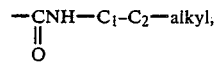

R$_8$ is C$_1$–C$_3$-alkyl,
R$_9$ is hydrogen,
R$_{10}$ is methyl,
R$_{11}$ is C$_1$–C$_2$-alkyl, whereby R$_{11}$'s together can also be C$_2$–C$_3$-alkylene,
R$_{12}$ is hydrogen, bromine, iodine or C$_1$–C$_2$-alkyl, and
X is oxygen.

Compounds of the last-mentioned group wherein R$_3$ is azido (—N$_3$) are particularly preferred active substances, especially those wherein Y is the group —CH(CH$_3$)COOCH$_3$ or

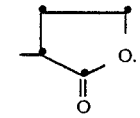

The following individual compounds are to be emphasised on account of their pronounced activity against phytopathogenic microorganisms:
N-(1'-methoxycarbonyl-ethyl)-N-methoxyacetyl-2-methyl-6-azido-aniline,
N-(tetrahydro-2'-on-fur-3'-yl)-n-methoxyacetyl-2,6-dimethyl-3-azido-aniline,
N-(1'-methoxycarbonyl-ethyl)-N-methoxyacetyl-2,6-dimethyl-3-azido-aniline,
N-(1'-methoxycarbonyl-ethyl)-N-(2-tetrahydrofurylcarbonyl)-2-methyl-6-azido-aniline,
N-(1'-methoxycarbonyl-3'-hydroxy-n-propyl)-N-methoxyacetyl-2-methyl-6-azido-aniline,
N-(1'-methoxycarbonyl-ethyl)-N-methylaminosulfonylacetyl-2,6-dimethyl-3-azido-aniline,
N-(1'-methoxycarbonyl-3-hydroxy-n-propyl)-N-cyclopropylcarbonyl-2-methyl-6-azido-aniline, N-(1'-methoxycarbonyl-ethyl)-N-methoxyacetyl-2,3-dimethyl-6-azido-aniline, N-(1'-cyanoethyl)-N-methoxyacetyl-2-methyl-6-azido-aniline, N-(1'-methyl-2'-dimethoxy-ethyl)-N-methoxyacetyl-2,6-dimethyl-3-azido-aniline, N-(2'-methyl-3'-methoximino-n-propyl)-N-methoxyacetyl-2-methyl-6-azido-aniline, N-(tetrahydro-2'-on-fur-3'-yl)-N-methoxyacetyl-2,3-dimethyl-4-azido-α-naphthylamine, N-(1'-cyano-ethyl)-N-methoxyacetyl-2,3-dimethyl-4-azido-α-naphthylamine, and N-(1'-cyanoethyl)-N-(2-tetrahydrofuryl-carbonyl)-2,3-dimethyl-4-azido-α-naphthylamine.

Phenylacylalanines having microbicidal activity and their production have already been known for some time from the literature. In this connection, there are mentioned for example the following publications: German Offenlegungsschriften Nos. 2,847,287, 2,908,739, 2,920,435, 2,922,759, 2,927,461 and 2,929,525, and also EP 5591, 12 703 and 17 850.

The compounds of the present invention are distinguished by a particularly uniform fungicidal activity, and by properties rendering them especially tolerant to plants.

The compounds of the formula I can be produced in a known manner, for example as described in the following. In the formulae II–VII, the symbols Ar, Y and $R_1$–$R_6$ have the meanings defined under the formula I. The symbol A denotes one of the usual removal groups, for example: alkoxy, benzenesulfonyloxy, p-bromobenzenesulfonyloxy, p-tosyloxy, trifluoroacetoxy, loweralkylsulfonyloxy, such as mesyloxy, or particularly halogen, such as fluorine, chlorine, bromine or iodine, preferably chlorine or bromine.

Production Process

Active substances of the formula I can be produced:
(A) by acylation of compounds of the formula II

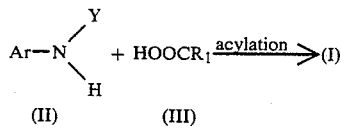

with carboxylic acids of the formula III or with reactive derivatives thereof; or (B) by reaction of compounds of the formula IV

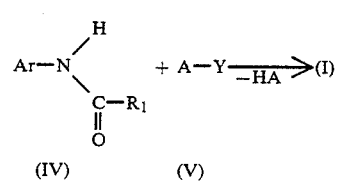

with compounds of the formula V, wherein A denotes a usual removal group; or, in the case where $R_3$ is the $N_3$ group, (C) by formation of the diazonium salts of the compounds of the formula VI, and subsequent variable reaction as follows:

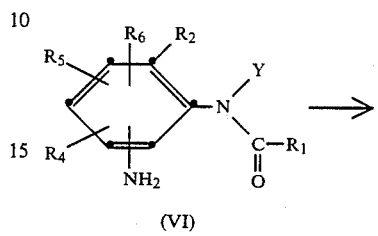

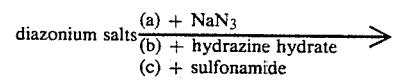

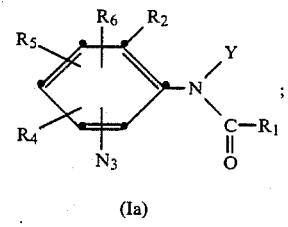

or, in the case where $R_3$ is the $HOCH_2$ group, (D) by reaction of compounds of the formula VII with NaOH in acetone

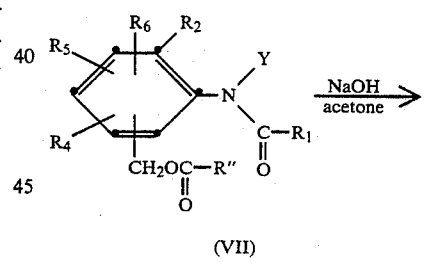

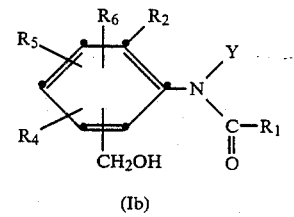

wherein R'' is $C_1$–$C_4$-alkyl; or, in the case where $R_3$ is one of the groups

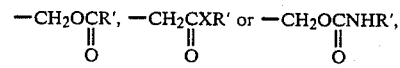

(E) by the following reactions of compounds of the formula Ib:

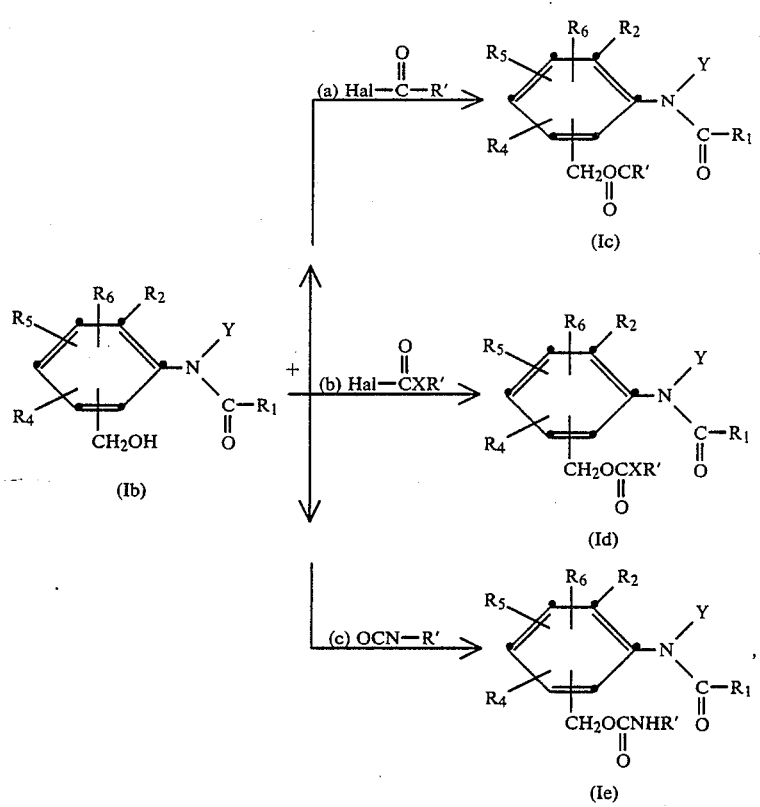

wherein "Hal" is halogen, preferably chlorine or bromine. In the case of reactions (a) and (b), they are preferably performed in the presence of an acid-binding agent.

The following reaction conditions are advantageous for the stated production processes:

Process A:

In this process is preferably used a reactive derivative of a compound of the formula III, for example the acid halide or acid anhydride or the ester. The acid chloride or the acid bromide is particularly suitable.

The reaction temperatures are between 0° and 180° C., preferably between 0° and 150° C., or at the boiling point of the solvent or solvent mixture. The use of acid-binding agents or of condensation agents is in some cases advantageous. Suitable as such are organic and inorganic bases, for example tertiary amines, such as trialkylamines (trimethylamine, triethylamine, tripropylamine, and so forth), pyridine and pyridine bases (4-dimethylaminopyridine, 4-pyrrolidylaminopyridine, and the like), oxides and hydroxides, carbonates and hydrogen carbonates of alkali metals and alkaline-earth metals, as well as alkali acetates.

Formed hydrogen halide can in some cases be expelled also by means of the passing through of inert gas, for example nitrogen, from the reaction mixture.

The N-acylation can be performed in the presence of solvents or diluents inert to the reactants. These are for example: aliphatic and aromatic hydrocarbons, such as chlorobenzene, methylene chloride, ethylene chloride, chloroform, carbon tetrachloride and tetrachloroethylene; ethers and ethereal compounds, such as dialkyl ether (diethyl ether, diisopropyl ether, tert-butyl methyl ether, and so forth), anisole, dioxane or tetrahydrofuran; nitriles, such as acetonitrile or propionitrile; N,N-dialkylated amides, such as dimethylformamide or dimethyl sulfoxide; ketones, such as acetone, diethyl ketone, methyl ethyl ketone, and mixtures of solvents of this kind with one another. The acylating agent itself can in some cases serve as solvent. The presence of a reaction catalyst, such as dimethylformamide, can be of advantage in performing acylation.

Process B:

The substituent A in the formula V is in this process one of the customary removal groups, for example alkoxy, benzenesulfonyloxy, p-bromobenzenesulfonyloxy, p-tosyloxy, trifluoroacetyloxy, lower-alkylsulfonyloxy, such as mesyloxy, or it is in particular halogen, such as fluorine, chlorine, bromine or iodine, preferably chlorine or bromine. In this embodiment, the starting compound of the formula IV is advantageously firstly converted, with butyllithium or sodium hydride, into the corresponding alkali salt, or alternatively the reaction is carried out in the presence of an acid-binding agent, in a manner analogous to that of variant A, preferably with the addition of catalytic amounts of alkali iodide.

Further methods for synthesis of compounds of the formula I are given for example at the following places in the literature: Houben-Weyl Vol. 11/2, p. 3 and Vol. 8, p.653.

Some of the starting materials for the production of the compounds of the formula I according to the invention are novel, whilst some are known. The novel starting materials can be produced by methods analogous to known methods. Applicable methods in this respect are described for examples at the following places in the literature: J. Org. Chem. 30, 4101 (1965); Tetrahedron 1967, 487; Tetrahedron 1967, 493; Org. Syntheses III, 650; Org. Syntheses III, 652; Org. Syntheses III, 710; and J. Org. Chem. 34, 3430 (1969).

Reference may be made in detail to some methods of production of starting materials. Thus, the starting materials for compounds of the formula I wherein $R_3$ is an $N_3$ group can be produced as follows:

nitration of compounds of the formula VIII with a reactive nitrating reagent to give compounds of the formula IX, and subsequent hydrogenation of the nitro compounds with a customary hydrogenating agent to obtain compounds of the formula VI:

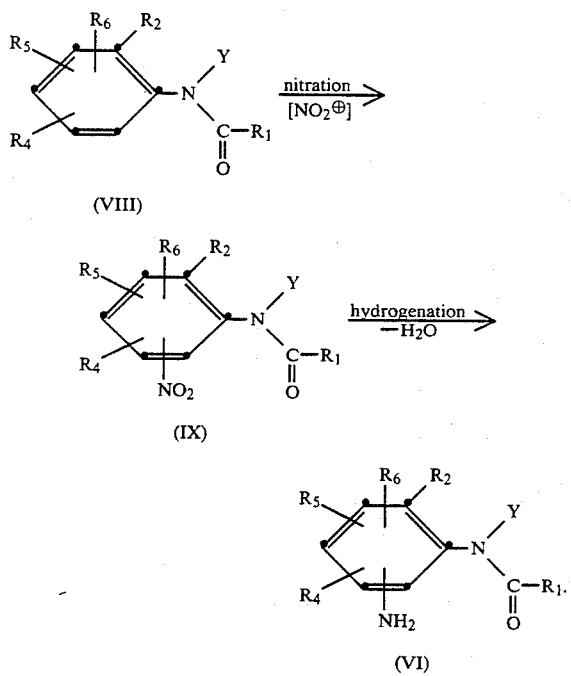

The compounds of the formula I contain in the molecule moiety Y at least one asymmetrical carbon atom. Racemates which are produced can be split into the optical antipodes by known methods of splitting racemates. The optical antipodes of the formula I have varying microbicidal activities.

There can be present depending on the manner of substitution further asymmetrical carbon atoms in the molecule of the compounds of the formula I.

Independently of the described optical isomerism in the compounds of the formula I, there is observed an atropisomerism around the aryl—$N<$ axis.

When no specific synthesis is carried out to isolate pure isomers, a product of the formula I is usually obtained as a mixture of these possible isomers.

It has been found that compounds of the formula I surprisingly exhibit a very favourable microbicidal spectrum for practical requirements. They can be used for example to protect cultivated plants.

The main field of application for compounds of the formula I is the combating of harmful microorganisms, particularly phytopathogenic fungi. The compounds of the formula I thus have for practical purposes a very favourable curative, preventive and systemic action for the protection of cultivated plants, without these becoming impaired as a result of undesirable side-effects. Cultivated plants within the scope of the present invention are for example: cereals (wheat, barley, rye, oats and rice); beet: (sugar beet and fodder beet); pomaceous fruit, stone fruit and soft fruit: (apples, pears, plums, peaches, almonds, cherries, strawberries, rasberries and blackberries); legumes: (beans, lentils, peas and soyabean); oil plants: (rape, mustard, poppy, olives, sunflowers, coco, castor-oil plants, cocoa and groundnuts); Cucurbitacea: (pumpkins, cucumbers and melons); fibre plants: (cotton, flax, hemp and jute); citrus fruits: (oranges, lemons, grapefruit and mandarins); varieties of vegetables: (spinach, lettuce, asparagus, varieties of cabbage, carrots, onions, tomatoes, potatoes and paprika); or plants such as maize, tobacco, nuts, coffee, sugar beet, tea, grapevines, hops, bananas and natural rubber plants; and also ornamental plants.

Microorganisms occurring on plants or on parts of plants (fruit, blossom, foliage, stalks, tubers or roots) of the said crops and of related cultivated crops can be inhibited or destroyed with the active substances of the formula I, and also parts of plants subsequently growing remain preserved from such microorganisms. The active substances are effective against the phytopathogenic fungi belonging to the following classes: against the Peronosporales (Phytophthora, Pythium and Plasmopara) belonging to the Oomycetes class, and also against the Ascomycetes, such as Erysiphe and *Venturia pathogens.*

Furthermore, the compounds of the formula I have a systemic action. They can also be used as dressing agents for the treatment of seed (fruits, tubers and grain), and of plant cuttings to protect them from fungus infections, and also against phytopathogenic fungi occurring in the soil.

The invention relates therefore also to the use of the compounds of the formula I for combating phytopathogenic microorganisms and/or for preventing infection on plants.

The compounds of the formula I are used either in an unmodified form or preferably together with auxiliaries customarily employed in formulation practice, and are thus processed in a known manner for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of composition, are selected to suit the objectives to be achieved and the given conditions.

Active substances of the formula I can be applied, simultaneously or successively, with further active substances to the surface or plant to be treated. These active substances can be fertilisers, trace-element agents or other preparations influencing plant growth. They can however also be selective herbicides, insecticides, fungicides, bactericides, nematocides or molluscicides, or mixtures of several of these preparations, optionally together with carriers, surface-active agents or additives facilitating application, which are customarily used in formulation practice.

The formulations, that is to say, the compositions or preparations containing the active substance of the formula I and optionally a solid or liquid additive, are produced in a known manner, for example by the intimate mixing and/or grinding of the active substances with extenders, such as with solvents, solid carriers and optionally surface-active compounds (tensides).

Suitable carriers and additives can be solid or liquid and correspond to the substances commonly used in formulation practice, such as natural or regenerated mineral substances, solvents, dispersing agents, wetting agents, adhesives, thickeners, binders or fertilisers.

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethylsulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers.

The surface-active agents (tensides) commonly used in formulation practice are described, inter alia, in the following publications: "Mc Cutcheon's Detergents and Emulsifiers Annual" MC Publishing Corp., Ringwood, N.J., 1980; and Sisely and Wood, "Encyclopedia of Surface Active Agents", Chemical Publishing Co., Inc. New York, 1980.

The pesticidal preparations contain as a rule 0.1 to 99, particularly 0.1 to 95, % by weight of active substance of the formula I, 1 to 99% by weight of a solid or liquid additive, and 0 to 25, especially 0.1 to 25, % by weight of a surface-active agent.

Whereas commercial products are preferably in the form of concentrated compositions, the compositions employed by the end-user are as a rule diluted.

The compositions can also contain further additives, such as stabilisers, antifoaming agents, viscosity regulators, binders and adhesives, as well as fertilisers, or other active substances for obtained special effects.

The invention relates also to compositions containing, as at least one active substance, a compound of the formula I, and to the use of the compositions for combating and/or preventing infestation by harmful microorganisms. The present invention embraces also the production of the compositions, this being characterised by the intimate mixing of the active substance with one or more of the substances or groups of substances described herein. Included also is a method of combating harmful microorganisms, which method comprises the application of the compounds of the formula I or of the novel compositions containing them.

The following Examples serve to further illustrate the present invention, without limiting the scope thereof. The temperature values are given in degrees Centigrade; and percentages and parts relate to weight. Except where otherwise stated, the isomeric mixture is meant in all cases where an active substance of the formula I is referred to.

EXAMPLE 1

Production of

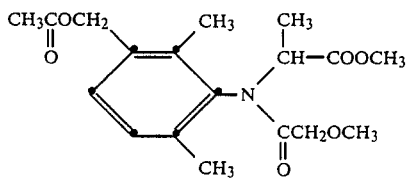

N-(1'-Methoxycarbonyl-ethyl)-N-methoxyacetyl-2,6-dimethyl-3-acetoxymethylaniline 35.0 g of N-(1'-methoxycarbonyl-ethyl)-2,6-dimethyl-3-acetoxymethylaniline and 13.3 g of sodium carbonate were placed into 250 ml of toluene, and 20.0 g of methoxyacetic acid chloride, dissolved in 50 ml of toluene, were slowly added. After the exothermic reaction had subsided, the temperature was held at 45° C. for 7 hours by means of a water-bath. The cooled reaction mixture was filtered, and the filtrate was concentrated in a rotary evaporator. The oily residue was distilled: b.p. 167°–171° C. at 0.07 bar.

EXAMPLE 2

Production of

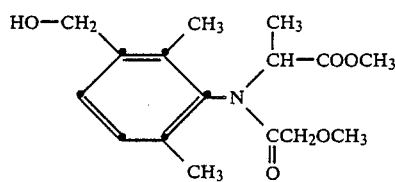

N-(1'-Methoxycarbonyl-ethyl)-N-methoxyacetyl-2,6-dimethyl-3-hydroxymethylaniline 23.0 g of N-(1'-methoxycarbonyl-ethyl)-N-methoxyacetyl-2,6-dimethyl-3-acetoxymethylaniline, 9.2 g of 30% sodium hydroxide solution and 100 ml of acetone were stirred for 3 hours at room temperature; 20 ml of water were then added, and the reaction mixture was extracted twice with 50 ml of diethyl ether each time. The combined ether extracts were dried over sodium sulfate, and the solvent was evaporated off. The oily crude product was chromatographed through a silica gel column by means of ether/chloroform (1:1) to thus obtain the product in the form of colourless oil: $n_D^{14} = 1.5352$.

EXAMPLE 3

Production of

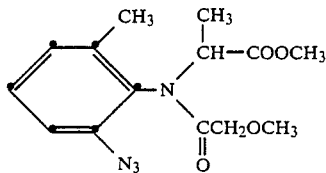

N-(1'-Methoxycarbonyl-ethyl)-N-methoxyacetyl-2-methyl-6-azidoaniline 10.0 g of N-(1'-methoxycarbonyl-ethyl)-N-methoxyacetyl-2-methyl-6-aminoaniline were stirred up with 75 g of ice and 15 ml of conc. hydrochloric acid at 0° to 5° C. until a clear solution was formed. At 0° to 5° C. were then added dropwise, within 10 minutes, 2.5 g of sodium nitrite dissolved in 10 ml of water. The reddish-brown solution was stirred for a further 30 minutes at the above temperature, and 100 ml of ether were subsequently added. There was thereupon added dropwise at 0° to 5° C., within 15 minutes, a solution of 2.5 g of sodium azide in 10 ml of water, and the temperature was allowed to rise in the course of 30 minutes to room temperature. The reaction mixture was extracted with ether; the organic phase was then washed with sodium hydrogen carbonate/water, dried with magnesium sulfate, and the solvent was evaporated off. The resulting oil was dried at 40° C. in vacuo; $n_D^{26}$:1.5396. $n_D^{28.5}$:1.5389.

EXAMPLE 4
Production of

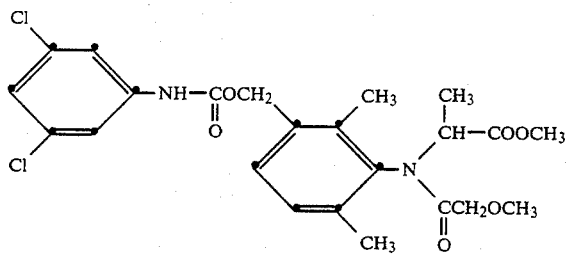

N-(1'-Methoxycarbonyl-ethyl)-N-methoxyacetyl-2,6-dimethyl-3-(3',5'-dichlorophenylcarbamoylmethyl)-aniline 16.2 g of N-(1'-methoxycarbonyl-ethyl)-2,6-dimethyl-3-(3',5'-dichlorophenylcarbamoylmethyl)-aniline and 3.2 g of pyridine were placed into 120 ml of toluene; and within 15 minutes were added 4.7 g of methoxyacetic acid chloride, dissolved in 30 ml of toluene. After the exothermic reaction had subsided, stirring was maintained for 4 hours at room temperature, and the reaction suspension was then filtered with suction. The yellow filtrate was washed with water, dried over sodium sulfate, and concentrated in a rotary evaporator. The solid residue was digested with ether, and the white crystals were filtered off with suction; m.p. 126°–128° C.

The following compounds of the formula I were produced in a manner analogous to that described in the foregoing.

TABLE 1.1
Compounds of the formula

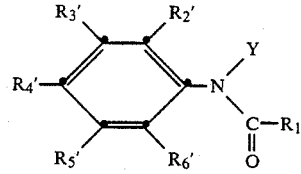

$R_4'$, $R_5'$ = H

| Comp. No. | $R_1$ | $R_2'$ | $R_3'$ | $R_6'$ | Y | Physical data |
|---|---|---|---|---|---|---|
| 1.1.1. | —CH$_2$OCH$_3$ | —CH$_3$ | —CH$_2$OCOCH$_3$ | —CH$_3$ | —CH(CH$_3$)—COOCH$_3$ | b.p. 167–171° C./ 0.07 mbar |
| 1.1.2. | —CH$_2$OCH$_3$ | —CH$_3$ | —CH$_2$OH | —CH$_3$ | —CH(CH$_3$)—COOCH$_3$ | $n_D^{14}$ = 1.5352 |
| 1.1.3. | —CH$_2$OCH$_3$ | —CH$_3$ | H | —N$_3$ | —CH(CH$_3$)—COOCH$_3$ | $n_D^{28.5}$ = 1.5389 |
| 1.1.4. | —CH$_2$OCH$_3$ | —CH$_3$ | —CH$_2$OCO—NH—(3,5-dichlorophenyl) | —CH$_3$ | —CH(CH$_3$)—COOCH$_3$ | m.p. 126–128° C. |
| 1.1.5. | —CH$_2$OCH$_3$ | —CH$_3$ | —N$_3$ | —CH$_3$ | (furanone ring) | m.p. 99–118° C. |
| 1.1.6. | —CH$_2$OCH$_3$ | —CH$_3$ | H | —CH$_2$OH | —CH(CH$_3$)—COOCH$_3$ | viscous oil |
| 1.1.7. | (furan ring) | —CH$_3$ | —CH$_2$OCOCH$_3$ | —CH$_3$ | —CH(CH$_3$)—COOCH$_3$ | viscous oil |

TABLE 1.1-continued

Compounds of the formula

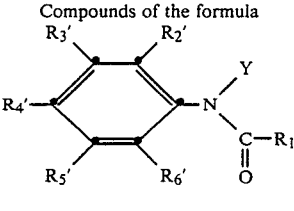

R4′, R5′ = H

| Comp. No. | R1 | R2′ | R3′ | R6′ | Y | Physical data |
|---|---|---|---|---|---|---|
| 1.1.8. | —CH2OCH3 | —CH3 | —CH2OCONH—CH(CH3)2 | —CH3 | —CH(CH3)—COOCH3 | viscous oil |
| 1.1.9. | —CH2OCH3 | —CH3 | —CH2OCOOCH3 | —CH3 | —CH(CH3)—COOCH3 | $n_D^{14}$ = 1.5172 |
| 1.1.10. | 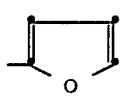 | —CH3 | —CH2OH | —CH3 | —CH(CH3)—COOCH3 | oil |
| 1.1.11. | —CH2OCH3 | —CH3 | —CH3 | —N3 | —CH(CH3)—COOCH3 | m.p. 80–82° C. |
| 1.1.12. | —CH2OCH3 | —CH3 | —N3 | —CH3 | —CH(CH3)—COOCH3 | m.p. 88–93° C. |
| 1.1.13. | —CH2OCH3 | —CH3 | H | —N3 | 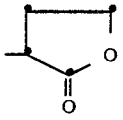 | |
| 1.1.14. | 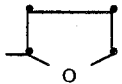 | —CH3 | H | —N3 | —CH(CH3)—COOCH3 | oil |
| 1.1.15. | 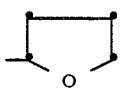 | —CH3 | H | —N3 | —CH(CH2CH2OH)—COOCH3 | |
| 1.1.16. | 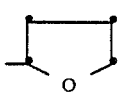 | —CH3 | —N3 | —CH3 | 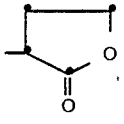 | |
| 1.1.17. | —CH2OCH3 | —CH3 | —N3 | OCH3 | —CH(CH3)—COOCH3 | |
| 1.1.18. | —CH2OCH3 | —CH3 | —N3 | —CH3 | —CH(CH2CH2OH)—COOCH3 | |
| 1.1.19. | —CH2OCH3 | —CH3 | H | —N3 | —CH(CH2—CH2OH)—COOCH3 | yellow oil |
| 1.1.20. | 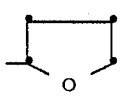 | —CH3 | H | —N3 | 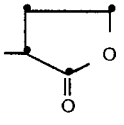 | |

TABLE 1.1-continued

Compounds of the formula $$\begin{array}{c} R_3' \quad R_2' \\ R_4' - C_6H_2 - N(Y) - C(=O) - R_1 \\ R_5' \quad R_6' \end{array}$$

$R_4', R_5' = H$

| Comp. No. | $R_1$ | $R_2'$ | $R_3'$ | $R_6'$ | Y | Physical data |
|---|---|---|---|---|---|---|
| 1.1.21. | oxetanyl (O in ring) | —CH₃ | —N₃ | —CH₃ | —CH(CH₃)—COOCH₃ | |
| 1.1.22. | oxetanyl (O in ring) | —CH₃ | —N₃ | —CH₃ | —CH(CH₂CH₂OH)—COOCH₃ | |
| 1.1.23. | —CH₂OCH₃ | —CH₃ | —N₃ | —OCH₃ | β-lactone (4-membered, C=O, O) | |
| 1.1.24. | —CH₂OCH₃ | —CH₃ | —N₃ | OCH₃ | —CH(CH₂—CH₂OH)—COOCH₃ | |
| 1.1.25. | —CH₂OSO₂NH—CH₃ | —CH₃ | —N₃ | —CH₃ | —CH(CH₃)—COOCH₃ | |
| 1.1.26. | —CH₂OSO₂NH—CH₃ | —CH₃ | —N₃ | —CH₃ | —CH(CH₂—CH₂OH)—COOCH₃ | |
| 1.1.27. | —CH=CH₂ | —CH₃ | H | —N₃ | β-lactone (4-membered, C=O, O) | |
| 1.1.28. | cyclopropyl | —CH₃ | H | —N₃ | β-lactone (4-membered, C=O, O) | |
| 1.1.29. | —CH₂—N(pyrazolyl) | —CH₃ | H | —N₃ | —CH(CH₃)—COOCH₃ | |
| 1.1.30. | oxetanyl (O in ring) | —CH₃ | —N₃ | —OCH₃ | —CH(CH₃)—COOCH₃ | |
| 1.1.31. | —CH₂OSO₂NH—CH₃ | —CH₃ | —N₃ | —CH₃ | β-lactone (4-membered, C=O, O) | |
| 1.1.32. | —CH(CH₃)—CH=CH | —CH₃ | H | —N₃ | —CH(CH₃)—COOCH₃ | |

TABLE 1.1-continued

Compounds of the formula $$\text{R}_3'\text{-}\text{R}_2'\text{-C}_6\text{H}\text{-}\text{R}_6'\text{-}\text{R}_5'\text{-N(Y)-C(=O)-R}_1$$

$R_4'$, $R_5'$ = H

| Comp. No. | $R_1$ | $R_2'$ | $R_3'$ | $R_6'$ | Y | Physical data |
|---|---|---|---|---|---|---|
| 1.1.33. | cyclopropyl | —CH$_3$ | H | —N$_3$ | —CH(CH$_3$)—COOCH$_3$ | |
| 1.1.34. | cyclopropyl | —CH$_3$ | H | —N$_3$ | CH$_2$—CH$_2$OH / —CH—COOCH$_3$ | m.p. 87–92° C. |
| 1.1.35. | —CH$_2$—N(1,2,4-triazolyl) | —CH$_3$ | H | —N$_3$ | γ-butyrolactonyl | |
| 1.1.36. | —CH$_2$—N(1,2,4-triazolyl) | —CH$_3$ | —N$_3$ | —CH$_3$ | —CH(CH$_3$)—COOCH$_3$ | |
| 1.1.37. | 2-tetrahydrofuryl | —CH$_3$ | —CH$_2$OCOCH$_3$ | —CH$_3$ | γ-butyrolactonyl | |
| 1.1.38. | —CH$_2$SO$_2$CH$_3$ | —CH$_3$ | —CH$_2$OCOCH$_3$ | —CH$_3$ | —CH(CH$_3$)—COOCH$_3$ | |
| 1.1.39. | —CH$_2$OC$_2$H$_5$ | —CH$_3$ | H | —N$_3$ | —CH(CH$_3$)—COOCH$_3$ | |
| 1.1.40. | —CH$_2$—N(pyrazolyl) | —CH$_3$ | —N$_3$ | —CH$_3$ | γ-butyrolactonyl | |
| 1.1.41. | —CH$_2$OSO$_2$NH(CH$_3$) | —CH$_3$ | —CH$_2$OCOCH$_3$ | —CH$_3$ | γ-butyrolactonyl | |
| 1.1.42. | —CH$_2$OCH$_2$—CH=CH$_2$ | —CH$_3$ | —CH$_2$OCOCH$_3$ | —CH$_3$ | —CH(CH$_3$)—COOCH$_3$ | |
| 1.1.43. | —CH$_2$OCH$_2$—CH=CH$_2$ | —CH$_3$ | H | —N$_3$ | γ-butyrolactonyl | |
| 1.1.44. | —CH$_2$OCH$_3$ | —CH$_3$ | —N$_3$ | —CH$_3$ | —CH(CH$_3$)—COO—i-C$_3$H$_7$ | |

TABLE 1.1-continued

Compounds of the formula

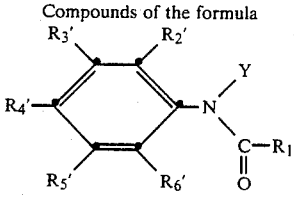

R4', R5' = H

| Comp. No. | R1 | R2' | R3' | R6' | Y | Physical data |
|---|---|---|---|---|---|---|
| 1.1.45. | —CH2OCH3 | —CH3 | —CH3 | —N3 | —CH(CH2CH2OCH3)—COOCH3 | |
| 1.1.46. |  | —CH3 | —N3 | —CH3 | —CH(CH3)—COOCH3 | m.p. 117–120° C. |
| 1.1.47. | —CH2OC2H5 | —CH3 | —N3 | —CH3 | —CH(CH3)—COOCH3 | |
| 1.1.48. | —CH2OCH3 | —Cl | H | —N3 | —CH(CH3)—COOCH3 | |
| 1.1.49. | 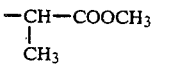 | —CH3 | —CH3 | —N3 | 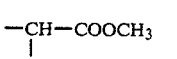 | |
| 1.1.50. | 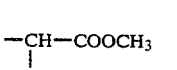 | —CH3 | —CH3 | —N3 | —CH(CH2CH2OH)—COOC2H5 | |
| 1.1.51. | —CH2S—P(=S)(OC2H5)2 | —CH3 | H | —N3 | —CH(CH3)—COOCH3 | |
| 1.1.52. | —CH2S—P(=O)(OCH3)2 | —CH3 | H | —N3 | 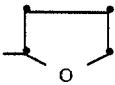 | |
| 1.1.53. | —CH2CH2OCH3 | —CH3 | —N3 | —CH3 | —CH(CH3)—COOCH3 | |
| 1.1.54. | —CH2OCH3 | —CH3 | H | —N3 | —CH(CH3)—CN | |
| 1.1.55. | 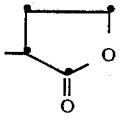 | —CH3 | H | —N3 | —CH(CH3)—CN | |
| 1.1.56. | —CH2S—P(=S)(OCH3)2 | —CH3 | H | —N3 | —CH(CH3)—COOCH3 | |
| 1.1.57. | —CH2S—P(=S)(OCH3)2 | —CH3 | —N3 | —CH3 | —CH(CH3)—COOCH3 | |
| 1.1.58. | —CH2OCOCH3 | —CH3 | H | —N3 | —CH(CH3)—COOCH3 | |

TABLE 1.1-continued

Compounds of the formula $$\text{R}_3'\text{-, R}_2'\text{-, R}_4'\text{-, R}_5'\text{-, R}_6'\text{-substituted phenyl-N(Y)-C(=O)-R}_1$$

$R_4'$, $R_5'$ = H

| Comp. No. | $R_1$ | $R_2'$ | $R_3'$ | $R_6'$ | Y | Physical data |
|---|---|---|---|---|---|---|
| 1.1.59. | —CH₂CH₂OCH₃ | —CH₃ | —N₃ | —CH₃ | (succinic anhydride-like ring: —CH—C(=O)—O—) | |
| 1.1.60. | —CH₂OCH₃ | —CH₃ | —N₃ | —CH₃ | —CH(CH₃)—CN | |
| 1.1.61. | —CH₂OCH₃ | —CH₃ | —N₃ | —CH₃ | —CH(CH₃)—CH(OCH₃)₂ | |
| 1.1.62. | —CH₂OCH₃ | —CH₃ | H | —N₃ | —CH₂—CH(CH₃)—CH=NOCH₃ | |
| 1.1.63. | (tetrahydrofuran-2-yl / oxolanyl) | —CH₃ | H | —N₃ | —CH(CH₃)—CH(OC₂H₅)₂ | |
| 1.1.64. | —CH₂OCH₃ | —CH₃ | H | —N₃ | —CH₂—C≡CH | |
| 1.1.65. | —CH₂OCH₃ | —CH₃ | —N₃ | —CH₃ | —CH₃—C≡CJ | |
| 1.1.66. | (tetrahydrofuran-2-yl) | —CH₃ | —N₃ | —CH₃ | —CH(CH₃)—CH=NOCH₃ | |
| 1.1.67. | —CH=CH—CH₃ | —CH₃ | —N₃ | —CH₃ | —CH(CH₃)—(1,3-dioxolan-2-yl) | |
| 1.1.68. | (tetrahydrofuran-2-yl) | —CH₃ | —N₃ | —CH₃ | —CH₂—C≡C—CH₃ | |
| 1.1.69. | —CH₂OCH₃ | —CH₃ | —CH₂OH | —CH₃ | —CH(CH₃)—CN | |
| 1.1.70. | —CH₂OC₂H₅ | —CH₃ | —CH₂OH | —CH₃ | —CH(CH₃)—COOCH₃ | |
| 1.1.71. | —CH₂OCH₃ | —CH₃ | —CH₂OH | —CH₃ | —CH(CH₃)—CH(OCH₃)₂ | |
| 1.1.72. | —CH₂OCH₃ | —CH₃ | —CH₃ | —CH₂OH | —CH(CH₃)—COOCH₃ | |

TABLE 1.1-continued

Compounds of the formula

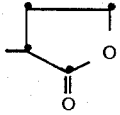

$R_4'$, $R_5'$ = H

| Comp. No. | $R_1$ | $R_2'$ | $R_3'$ | $R_6'$ | Y | Physical data |
|---|---|---|---|---|---|---|
| 1.1.73. | —CH$_2$OCH$_3$ | —CH$_3$ | —CH$_2$OH | —CH$_3$ | (oxetanone ring) | |
| 1.1.74. | —CH$_2$OCH$_3$ | —CH$_3$ | —CH$_2$OH | —CH$_3$ | —CH(CH$_3$)—CH=N—OH | |
| 1.1.75. | —CH$_2$OCH$_3$ | —CH$_3$ | —CH$_2$OH | —CH$_3$ | —CH(CH$_3$)—CH=N—OCH$_3$ | |
| 1.1.76. | —CH$_2$OCH$_3$ | —Cl | H | —CH$_2$OH | —CH(CH$_3$)—COOCH$_3$ | |

TABLE 1.2

Compounds of the formula:

| Comp. No. | $R_1$ | $R_2'$ | $R_3'$ | $R_4'$ | $R_5'$ | $R_6'$ | Y | Physical data |
|---|---|---|---|---|---|---|---|---|
| 1.2.1. | —CH$_2$OCH$_3$ | —CH$_3$ | —CH$_3$ | —N$_3$ | —CH$_3$ | —CH$_3$ | —CH(CH$_3$)—COOCH$_3$ | |
| 1.2.2. | —CH$_2$O—i-C$_3$H$_7$ | —CH$_3$ | —CH$_3$ | —N$_3$ | —CH$_3$ | —CH$_3$ | —CH(CH$_3$)—COOCH$_3$ | |
| 1.2.3. | —CH$_2$OCH$_3$ | —CH$_3$ | —CH$_3$ | —N$_3$ | —CH$_3$ | —CH$_3$ | —CH(CH$_3$)—COO—i-C$_3$H$_7$ | |
| 1.2.4. | (dioxolane) | —CH$_3$ | —CH$_3$ | —N$_3$ | —CH$_3$ | —CH$_3$ | (oxetanone ring) | |
| 1.2.5. | —CH$_2$SO$_2$CH$_3$ | —CH$_3$ | —CH$_3$ | —N$_3$ | —CH$_3$ | —CH$_3$ | —CH(CH$_3$)—COOCH$_3$ | |

TABLE 2.1

Compounds of the formula $R_4' = H$

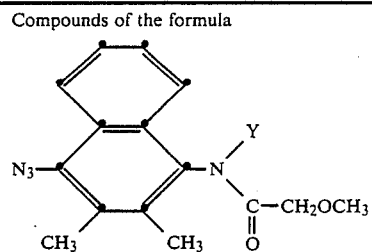

| Comp. No. | $R_3'$ | $R_5'$ | Y | Physical data |
|---|---|---|---|---|
| 2.1.1. | $-N_3$ | H | $-CH(CH_3)-COOCH_3$ | resin |
| 2.1.2. | $-CH_3$ | $-N_3$ | $-CH(CH_3)-COOCH_3$ | |
| 2.1.3. | $-N_3$ | H | (butyrolactone ring) | |
| 2.1.4. | $-CH_2OH$ | H | $-CH(CH_3)-CN$ | |
| 2.1.5. | $-CH_3$ | $-N_3$ | $-CH(CH_3)-CH=NOH$ | |
| 2.1.6. | $-N_3$ | H | $-CH(CH_3)-C\equiv CH$ | |
| 2.1.7. | $-CH_3$ | $-N_3$ | (butyrolactone ring) | |
| 2.1.8. | $-CH_2OCOCH_3$ | $-NO_2$ | $-CH(CH_3)-COOCH_3$ | |
| 2.1.9. | $-CH_3$ | $-N_3$ | $-CH(CH_3)-CN$ | |
| 2.1.10. | $-N_3$ | H | $-CH(CH_3)-CH(OCH_3)_2$ | |

TABLE 2.2

Compounds of the formula (naphthyl with $N_3$, two $CH_3$, $N(Y)COCH_2OCH_3$)

| Comp. No. | Y | Physical data |
|---|---|---|
| 2.2.1. | $-CH(CH_3)-COOCH_3$ | |
| 2.2.2. | (butyrolactone ring) | m.p. 45–57° C. |
| 2.2.3. | $-CH(CH_3)-CN$ | |
| 2.2.4. | $-CH(CH_3)-CH=NOH$ | |
| 2.2.5. | $-CH(CH_3)-CH(OCH_3)_2$ | |
| 2.2.6. | $-CH((CH_2)_2OH)-COOCH_3$ | |
| 2.2.7. | $-CH(CH_3)-C\equiv CH$ | |

TABLE 2.3

Compounds of the fromula

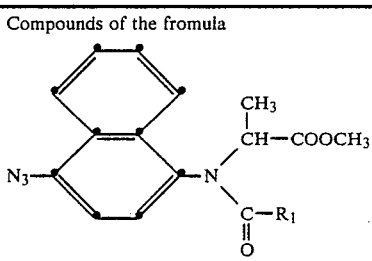

| Comp. No. | $R_1$ | Physical data |
|---|---|---|
| 2.3.1. | $-CH_2OC_2H_5$ | m.p. 93–96° C. |
| 2.3.2. | (furyl) | |
| 2.3.3. | (cyclopropyl) | |
| 2.3.4. | $-CH_2-N$(triazole) | |

TABLE 2.3-continued

Compounds of the formula

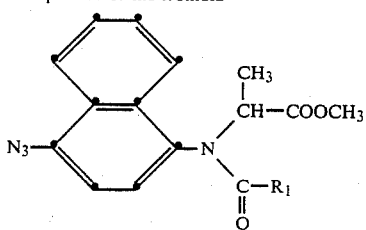

| Comp. No. | R₁ | Physical data |
|---|---|---|
| 2.3.5. | —CH₂OSO₂NH—CH₃ | |
| 2.3.6. | —CH₂SO₂CH₃ | |
| 2.3.7. | —CH₂CH₂OCH₃ | |

TABLE 2.4

Compounds of the formula

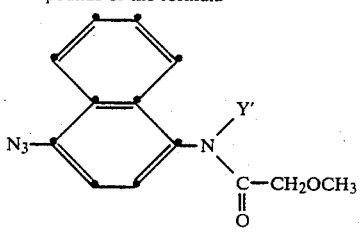

| Comp. No. | Y' | Physical data |
|---|---|---|
| 2.4.1. | —CH₂CN | wax-like substance |
| 2.4.2. | —CH₂CH(OCH₃)₂ | viscous oil |
| 2.4.3. | —CH₂C≡CH | m.p. 57–63° C. |

BIOLOGICAL EXAMPLES

The compositions used in the following Examples are formulated in the manner described in the subsequent formulation examples.

EXAMPLE 5

Action against *Phytophthora infestans* on tomato plants (a) Residual protective action After 3-weeks' cultivation, tomato plants were sprayed with a spray liquor produced from wettable powder of the active substance (0.02% of active substance). After 24 hours, the treated plants were infested with a suspension of sporangia of the fungus. An assessment of the fungus infection was made after incubation of the infested plants during 5 days at 20° C. with 90–100% relative humidity.

Compared with the fungus infection occurring on the control plants (100% infection), the infection on tomato plants treated with any one of the compounds Nos. 1.1.1, 1.1.2, 1.1.3, 1.1.4, 1.1.5, 1.1.7, 1.1.9, 1.1.10, 1.1.12, 1.1.14, 1.1.19, 1.1.34, 1.1.61 and 1.1.62, and Nos. 2.2.1, 2.2.2 and 2.2.3 was reduced to less than 10%.

(b) Systemic action

A spray liquor prepared from wettable powder of the active substance (0.006% of active substance, relative to the volume of soil) was applied to the soil in which tomato plants had been cultivated for 3 weeks. Care was taken to ensure that the spray liquor did not come into contact with the parts of the plants above the soil. After 48 hours, the treated plants were infested with a suspension of sporangia of the fungus. An assessment of fungus infection was made after incubation of the infested plants during 5 days at 20° C. with 90–100% relative umidity.

Compounds exhibiting in the above test a very good systemic action were, inter alia: Compounds Nos. 1.1.1, 1.1.2, 1.1.3, 1.1.5, 1.1.9, 1.1.10, 1.1.12, 1.1.14, 1.1.19, 1.1.34, 1.1.54 and 1.1.61, and also No. 2.2.1 and No. 2.2.2. Compared with fungus infection occuring on the untreated but infested control plants (100% infection), the infection on tomato plants treated with any one of the these compounds had been almost completely eliminated (0 to 5%).

(c) Residual curative action

After 3-weeks' cultivation, tomato plants were infested with a suspension of sporangia of the fungus. After an incubation time of 22 hours in a moist chamber at 20°C. with 90°–100° relative humidity, the infested plants were dried, and then sprayed with a spray liquor prepared from wettable powder of the active substance (0.06% of active substance). After the drying of the applied coating, the treated plants were returned to the moist chamber. An assessment of fungus infection was made 5 days after infestation.

Compared with fungus infection occurring on the untreated but infested control plants (100% infection), the infection on tomato plants treated with any one of the Compounds Nos. 1.1.1, 1.1.2, 1.1.3, 1.1.10, 1.1.12, 1.1.14, 1.1.19, 1.1.34 and 1.1.61 and Nos. 2.2.1, 2.2.2 and 2.2.3 was less than 10%.

EXAMPLE 6

Residual protective action against *Venturia inaequalis* on apple shoots

Apple seedlings having 10–20 cm long fresh shoots were sprayed with a spray liquor prepared from wettable powder of the active substance (0.06% of active substance). The treated plants were sprayed after 24 hours with a conidiospore suspension of the fungus. The plants were then incubated for 5 days with 90–100% relative humidity, and for a further 10 days they were kept at 20°–24° C. in a greenhouse. The extent of scab infection was assessed 15 days after infestation. The occurrence of the disease was reduced to 10 to 15% by, inter alia: the compounds Nos. 1.1.1, 1.1.2, 1.1.10, 1.1.37, 1.1.42, 1.1.69, 2.1.1, 2.1.4 and 2.1.8.

EXAMPLE 7

Action against *Pythium debaryanum* on sugar beet plants (a) Effect after soil application The fungus was cultivated on a carrot-chips nutrient solution, and was then added to a soil/sand mixture. The soil infested in this manner was placed into flower pots, and sown with sugar-beet seeds. Immediately after the sowing, the test preparation prepared from wettable powder was poured, as an aqueous suspension, over the soil (20 ppm of any one of the compounds in the Tables 1 and 2, relative to the volume of soil). Th pots were then placed for 2–3 weeks in a greenhouse at about 20° C. The soil was maintained during this period uniformly moist by light watering. In the evaluation of the test, the sprouting of the sugar-beet plants and the proportion of healthy plants and of diseased plants were assessed.

(b) Effect after dressing application

The fungus was cultivated on a carrot-chips nutrient solution, and applied to a soil/sand mixture. The soil infested in this manner was placed into soil trays, and sown with sugar-beet seeds which had been dressed with the test preparations formulated as dressing powder (0.06% of any one of the compounds in Tables 1 and 2). The sown trays were left for 2-3 weeks in a greenhouse at about 20+ C. The soil was maintained uniformly moist by light spraying. In the assessment of the test results, the extent of sprouting of the sugar-beet plants was determined.

The compounds Nos. 1.1.1, 1.1.2, 1.1.3, 1.1.5, 1.1.7, 1.1.9, 1.1.10, 1.1.12, 1.1.14, 1.1.19, 1.1.25, 1.1.34, 1.1.54, 1.1.61 and 1.1.62 and Nos. 2.2.1, 2.2.2 and 2.2.3 were completely effective against Pythium pathogens (over 90% of plants had sprouted) in both tests (a) and (b). The plants had a healthy appearance.

An equally good effect was achieved in analogous tests against Phythium pathogens on maize plants.

EXAMPLE 8

Action against *Podosphaera leucotricha* on apple seedlings

Residual protective action

Apple seedlings having about 5 developed leaves were sprayed with a spray liquor prepared from wettable powder of the active substance (0.06% of active substance). After 24 hours, the treated plants were infested with a conidiospore suspension of the fungus, and were transferred to a controlled atmosphere chamber at 20° with 70% relative humidity. The assessment of fungus infection was made 12 days after infestation.

Compared with fungus infection occurring on the untreated but infested apple seedings (100% infection), the infection on apple seedlings treated with any one of the compounds Nos. 1.1.1, 1.1.2, 1.1.3, 1.1.4, 1.1.5, 1.1.7, 1.1.9, 1.1.10, 1.1.14, 1.1.19, 1.1.25, 1.1.34, 1.1.54, 1.1.61, and 1.1.62 and Nos. 2.2.1, 2.2.2 and 2.2.3 was less than 10%.

| Formulation examples for liquid active substances of the formula I (% = percent by weight) | | | |
|---|---|---|---|
| Example 9 Emulsion concentrates | (a) | (b) | (c) |
| active substance from Tables 1.1-2.4 | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20%. |

Emulsions of any required concentration can be produced from such concentrates by dilution with water.

| Example 10 Solutions | (a) | (b) | (c) | (d) |
|---|---|---|---|---|
| active substance from Tables 1.1-2.4 | 80% | 10% | 5% | 95% |
| ethylene glycol-monomethyl ether | 20% | — | — | — |
| polyethylene glycol MG 400 | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | —. |

The solutions are suitable for application in the form of very fine drops.

| Example 11 Granulates | (a) | (b) |
|---|---|---|
| active substance from Tables 1.1-2.4 | 5% | 10% |
| kaolin | 94% | — |
| highly dispersed silicic acid | 1% | — |
| attapulgite | — | 90%. |

The active substance is dissolved in methylene chloride, the solution is sprayed onto the carrier, and the solvent is subsequently evaporated off in vacuo.

| Example 12 Dusts | (a) | (b) |
|---|---|---|
| active substance from Tables 1.1-2.4 | 2% | 5% |
| highly dispersed silicic acid | 1% | 5% |
| talcum | 97% | — |
| kaolin | — | 90%. |

Ready-for-use dusts are obtained by the intimate mixing together of the carriers with the active substance.

| Formulation examples for solid active substances of the formula I (% = percent by weight) | | | |
|---|---|---|---|
| Example 13 Wettable powders | (a) | (b) | (c) |
| active substance from Tables 1.1-2.4 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7–8 mols of ethylene oxide) | — | 2% | — |
| highly dispersed silicic acid | 5% | 10% | 10% |
| kaolin | 62% | 27% | — |

The active substance is well mixed with the additives and the mixture is thoroughly ground in a suitable mill. Wettable powders which can be diluted with water to give suspensions of the required concentration are obtained.

| Example 14 Emulsion concentrate | |
|---|---|
| active substance from Tables 1.1-2.4 | 10% |
| octylphenolpolyethylene glycol ether (4–5 mols of ethylene oxide) | 3% |
| calcium dodecylbenzenesulfonate | 3% |
| castor oil polyglycol ether (36 mols of ethylene oxide) | 4% |
| cyclohexanone | 30% |
| xylene mixture | 50%. |

Emulsions of the required concentration can be obtained from this concentrate by dilution with water.

| Example 15 Dusts | (a) | (b) |
|---|---|---|
| active substance from Tables 1.1-2.4 | 5% | 8% |
| talcum | 95% | — |
| kaolin | — | 92%. |

Dusts ready for use are obtained by mixing the active substance with the carriers and grinding the mixture in a suitable mill.

| Example 16 Extruder granulate | |
|---|---|
| active substance from Tables 1.1-2.4 | 10% |
| sodium lignin sulfonate | 2% |
| carboxymethylcellulose | 1% |
| kaolin | 87%. |

The active substance is mixed and ground with the additives, and the mixture is moistened with water. This mixture is then extruded and dried in a stream of air.

| Example 17 Coated granulate | |
|---|---|
| active substance from Tables 1.1–2.4 | 3% |
| polyethylene glycol (MG 200) | 3% |
| kaolin | 94%. |

The finely ground active substance is evenly applied, in a mixer, to the kaolin moistened with polyethylene glycol. Dustfree coated granules are obtained in this manner.

| Example 18 Suspension concentrate | |
|---|---|
| active substance from Tables 1.1–2.4 | 40% |
| ethylene glycol | 10% |
| nonylphenolpolyethylene glycol ether (15 mols of ethylene oxide) | 6% |
| sodium lignin sulfonate | 10% |
| carboxymethyl cellulose | 1% |
| 37% aqueous formaldehyde solution | 0.2% |
| silicone oil in the form of a 75% aqueous emulsion | 0.8% |
| water | 32%. |

The finely ground active substance is intimately mixed with the additives. There is thus obtained a suspension concentrate from which can be prepared, by dilution with water, suspensions of the concentration required.

What is claimed is:

1. A compound of the formula I

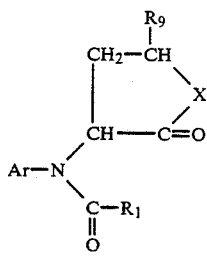

wherein
Ar is a group of the formula

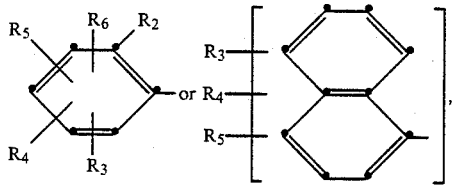

$R_1$ is 2-furyl, 2-tetrahydrofuryl, $C_2$–$C_4$-alkenyl, cyclopropyl, $\beta$-($C_1$–$C_4$)-alkoxyethyl or —$CH_2Z$, each being unsubstituted or substituted by halogen, and Z being
(a) —OH,
(b) —1H-1,2,4-triazolyl, 1-imidazolyl or 1-pyrazolyl,
(c) —S(O)$_n$—R$_{13}$, where R$_{13}$ is $C_1$–$C_4$-alkyl, and n is 1 or 2,
(d) —X—R$_{14}$, where X is oxygen or sulfur, and R$_{14}$ is $C_1$–$C_6$-alkyl, $C_3$–$C_4$-alkenyl or $C_3$–$C_4$-alkynyl, each unsubstituted or substituted by $C_1$–$C_2$-alkoxy,
(e) —OSO$_2$—R$_{15}$, where R$_{15}$ is $C_1$–$C_4$-alkyl, or mono- or di-($C_1$–$C_3$)-alkylamine,

where X is oxygen or sulfur, R$_{16}$ is $C_1$–$C_4$-alkyl, $C_1$–$C_4$-alkoxy or $C_1$–$C_4$-alkylamino, and R$_{17}$ is $C_1$–$C_4$-alkoxy or $C_1$–$C_4$-alkylamino, or

where R$_{18}$ is $C_1$–$C_3$-alkyl which is unsubstituted or substituted by $C_1$–$C_2$-alkoxy,
R$_2$ is $C_1$–$C_3$-alkyl, $C_1$–$C_3$-alkoxy or halogen,
R$_3$ is —CH$_2$OH, —N$_3$,

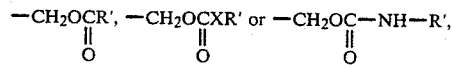

where R' is $C_1$–$C_6$-alkyl or $C_2$–$C_4$-alkenyl, each unsubstituted or substituted by halogen or $C_1$–$C_3$-alkoxy, or it is phenyl substituted by chlorine and X is oxygen or sulfur,
R$_4$ is hydrogen, $C_1$–$C_3$-alkyl, $C_1$–$C_3$-alkoxy, halogen, —NO$_2$ or —NH$_2$,
R$_5$ is hydrogen or $C_1$–$C_3$-alkyl,
R$_6$ is hydrogen or $C_1$–$C_3$-alkyl,
R$_9$ is hydrogen or methyl,
X is oxygen or sulfur.

2. A compound according to claim 1, wherein
R$_1$ is 2furyl, 2-tetrahydrofuryl, C$_2$–C$_4$-alkenyl, cyclopropyl, $\beta$-($C_1$–$C_2$)-alkoxyethyl or CH$_2$—Z, where Z is
(a) —OH,
(b) 1H-1,2,4-triazolyl or 1-imidazolyl,
(c) —S(O)$_n$—R$_{13}$, where R$_{13}$ is $C_1$–$C_2$-alkyl, and n is 2,
(d) —X'—R$_{14}$, where X' is oxygen or sulfur, and R$_{14}$ is $C_1$–$C_6$-alkyl, $C_3$–$C_4$-alkenyl or $C_3$–$C_4$-alkynyl, each unsubstituted or substituted by $C_1$–$C_2$-alkoxy,
(e) —OSO$_2$—R$_{15}$, where R$_{15}$ is $C_1$–$C_2$-alkyl, or mono, or di-($C_1$–$C_2$)-alkylamine,

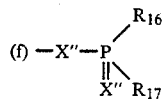

where X" is sulfur, R$_{16}$ is $C_1$–$C_2$-alkyl, $C_1$–$C_4$-alkoxy or $C_1$–$C_2$-alkylamino, and R$_{17}$ is $C_1$–$C_4$-alkoxy or $C_1$–$C_4$-alkylamino, or

where R$_{18}$ is $C_1$–$C_2$-alkyl which is unsubstituted or substituted by $C_1$–$C_2$-alkoxy,
R$_2$ is $C_1$–$C_2$-alkyl, $C_1$–$C_2$-alkoxy or halogen, $R_3$ is $-CH_2OH$, $-N_3$, $-CH_2OC(=O)-R'$, $-CH_2OCX'''(=O)-R'$ or $-CH_2OCNH(=O)-R'$, where R' is $C_1-C_3$-alkyl or $C_2-C_3$-alkenyl, each unsubstituted or substituted by chlorine or methoxy, and X''' is oxygen or sulfur, $R_4$ is hydrogen, $C_1-C_2$-alkyl, $C_1-C_2$-alkoxy, $-NO_2$ or $-NH_2$, $R_5$ is hydrogen or $C_1-C_2$-alkyl, $R_6$ is hydrogen or $C_1-C_2$-alkyl, $R_9$ is hydrogen.

3. A compound according to claim 2, wherein
$R_1$ is 2-furyl, 2-tetrahydrofuryl, $C_2-C_4$-alkenyl, cyclopropyl, 4-methoxyethyl or $-CH_2Z$, where Z is
 (a) 1H-1,2,4-triazolyl,
 (b) $-S(O)_n-R_{13}$, where $R_{13}$ is $CH_3$, and n is 2,
 (c) $-X'^v-R_{14}$, where $X'^v$ is oxygen, and $R_{14}$ is $C_1-C_4$-alkyl, $C_3-C_4$-alkenyl or $C_3-C_4$-alkynyl, each unsubstituted or substituted by $C_1-C_2$-alkoxy,
 (d) $-OSO_2-R_{15}$, where $R_{15}$ is mono-$(C_1-C_3)$-alkylamine, (e) $-X^v-P(=X^v)(R_{16})(R_{17})$ where $X^v$ is sulfur, and $R_{16}$ and $R_{17}$ independently of one another are each $C_1-C_3$-alkoxy, or (f) $-OC(=O)-R_{18}$ where $R_{18}$ is $C_1-C_3$-alkyl, $R_2$ is methyl, methoxy or chlorine, $R_3$ is $-CH_2OH$, $-N_3$ or $-CH_2OCCH_3(=O)$ $R_4$ is hydrogen, methyl, methoxy, $NO_2$ or $NH_2$, $R_5$ is hydrogen or methyl, $R_6$ is hydrogen or methyl, $R_9$ is hydrogen, X is oxygen.

4. A compound according to claim 3, wherein $R_3$ is the azido group ($-N_3$).

5. A compound according to claim 4, selected from the group of the following azido compounds:
N-(tetrahydro-2'-on-fur-3'-yl)-N-methoxyacetyl-2,6-dimethyl-3azido-aniline, and
N-(tetrahydro-2'-on-fur3'-yl)-N-methoxyacetyl-2,3-dimethyl-4-azido-α-naphthylamine.

6. A composition for combating and/or preventing an infestation by harmful microorganisms, which composition contains as active ingredient at least one active substance according to claim 1 and an inert carrier.

7. A composition according to claim 6, which contains 0.1 to 99 percent by weight of the active substance 1 to 99 percent by weight of additives, and 0 to 25 percent by weight of a surface-active agent.

8. A composition according to claim 7, which contains 0.1 to 95 percent by weight of the active substance.

9. A composition according to claim 8, which contains 0.1 to 25 percent by weight of a surface-active agent.

10. A process for combating and/or preventing an infestation of plants by phytopathogenic microorganisms, which process comprises applying an effective amount of a compound according to any one of claims 1 to 4 and 5, in diluted form, to the plants or to the locus thereof.

11. A process for combating and/or preventing an infestation of plants by phytopathogenic fungi, which process comprises applying a fungicidally effective amount of a compound according to any one of claims 1 to 4 and 5, in diluted form, to the plants or to the locus thereof.

* * * * *